US00PP32471P2

(12) United States Plant Patent
Schroll

(10) Patent No.: US PP32,471 P2
(45) Date of Patent: Nov. 17, 2020

(54) ***HYDRANGEA* PLANT NAMED 'SCHROLL66-11-01'**

(50) Latin Name: *Hydrangea macrophylla*
Varietal Denomination: SCHROLL66-11-01

(71) Applicant: Soren Schroll, Odense SV (DK)

(72) Inventor: Soren Schroll, Odense SV (DK)

(73) Assignee: SCHROLL MANAGEMENT ApS, Odense SV (DK)

( * ) Notice: Subject to any disclaimer, the term of this patent is extended or adjusted under 35 U.S.C. 154(b) by 0 days.

(21) Appl. No.: 16/873,041

(22) Filed: Jan. 21, 2020

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — C. A. Whealy

(57) ABSTRACT

A new and distinct cultivar of *Hydrangea* plant named 'SCHROLL66-11-01', characterized by its compact, upright and mounded plant habit; moderately vigorous growth habit; freely branching habit and strong stems; dark green-colored leaves; mophead-type inflorescences with light red purple-colored sterile flowers; when "blued", that is, treated with aluminum sulfate, sterile flowers are light violet blue in color; long flowering period; and good postproduction quality and longevity.

3 Drawing Sheets

Figure 1:
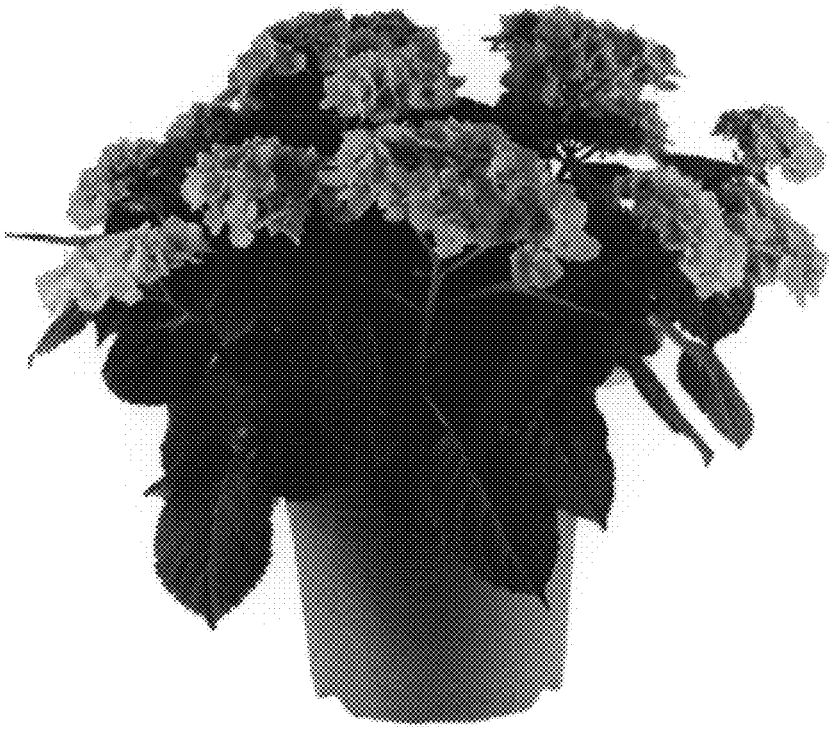

Botanical designation: *Hydrangea macrophylla.*
Cultivar denomination: 'SCHROLL66-11-01'.

BACKGROUND OF THE INVENTION

The present invention relates to a new and distinct cultivar of *Hydrangea* plant, botanically known as *Hydrangea macrophylla* and hereinafter referred to by the name 'SCHROLL66-11-01'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant originated from a cross-pollination during the spring of 2011 of a proprietary selection of *Hydrangea macrophylla* identified as code number 36-00, not patented, as the female, or seed, parent with a proprietary selection of *Hydrangea macrophylla* identified as code number 083001, not patented, as the male, or pollen, parent. The new *Hydrangea* plant was discovered and selected by the Inventor in February, 2013 as a flowering plant from within the progeny of the stated cross-pollination in a controlled greenhouse environment in Aarslev, Denmark.

Asexual reproduction of the new cultivar by softwood cuttings in Aarslev, Denmark since the spring of 2013 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL66-11-01'. These characteristics in combination distinguish 'SCHROLL66-11-01' as a new and distinct *Hydrangea* plant:

1. Compact, upright and mounded plant habit.
2. Moderately vigorous growth habit.
3. Freely branching habit and strong stems.
4. Dark green-colored leaves.
5. Mophead-type inflorescences with light red purple-colored sterile flowers; when "blued", that is, treated with aluminum sulfate, sterile flowers are light violet blue in color.
6. Long flowering period.
7. Good postproduction quality and longevity.

Plants of the new *Hydrangea* differ primarily from plants of the female selection parent in the following characteristics:

1. Plants of the new *Hydrangea* are more compact than and not as vigorous as plants of the female parent selection.
2. Inflorescences of plants of the new *Hydrangea* are denser and sturdier than inflorescences of plants of the female parent selection.
3. Plants of the new *Hydrangea* and the female parent selection differ in sterile flower color as sterile flowers of plants of the new *Hydrangea* are brighter than and not as pale as sterile flowers of plants of the female parent selection.

Plants of the new *Hydrangea* differ primarily from plants of the male selection parent in sterile flower color as sterile flowers of plants of the new *Hydrangea* are lighter in color than plants of the male parent selection. In addition, margins of sterile flowers of plants of the new *Hydrangea* are more crenate than margins of sterile flowers of plants of the male parent selection.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the *Hydrangea* are more compact than and not as vigorous as plants of 'H213901'.
2. Plants of the *Hydrangea* grow more slowly than plants of 'H213901'.
3. Sepals of sterile flowers of the new *Hydrangea* are not as undulate as sepals of sterile flowers of 'H213901'.
4. Plants of the new *Hydrangea* and 'H213901' differ in sterile flower color as sterile flowers of plants of the new *Hydrangea* are lighter red purple in color than sterile flowers of plants of 'H213901'.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in sterile flower color as sterile flowers of plants of the new *Hydrangea* are lighter in color than sterile flowers of plants of 'H213906'. In addition, inflorescences of plants of the new *Hydrangea* are longer-lasting than inflorescences of plants of 'H213906'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 3) comprises a side perspective view of a typical flowering plant of 'SCHROLL66-11-01' grown in a container that has not been "blued".

Figure 2:
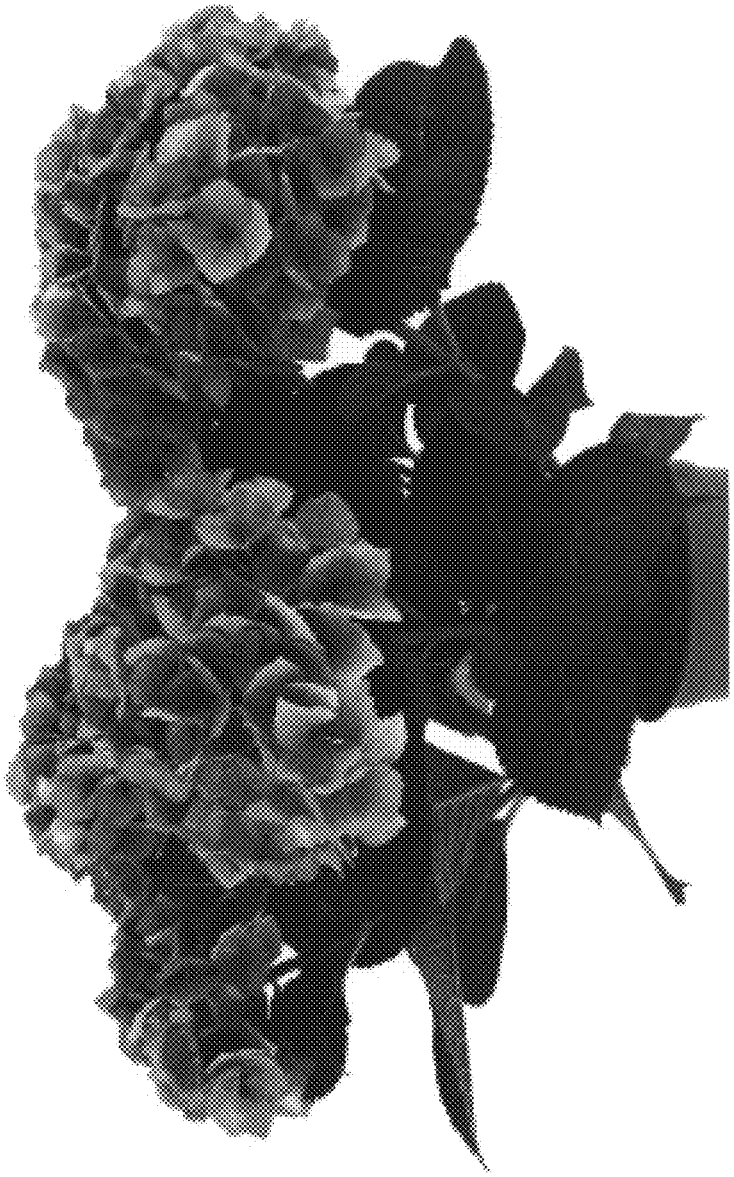

The photograph on the second sheet (FIG. 2 of 3) is a close-up view of a typical inflorescence of 'SCHROLL66-11-01' that has been "blued".

Figure 3:
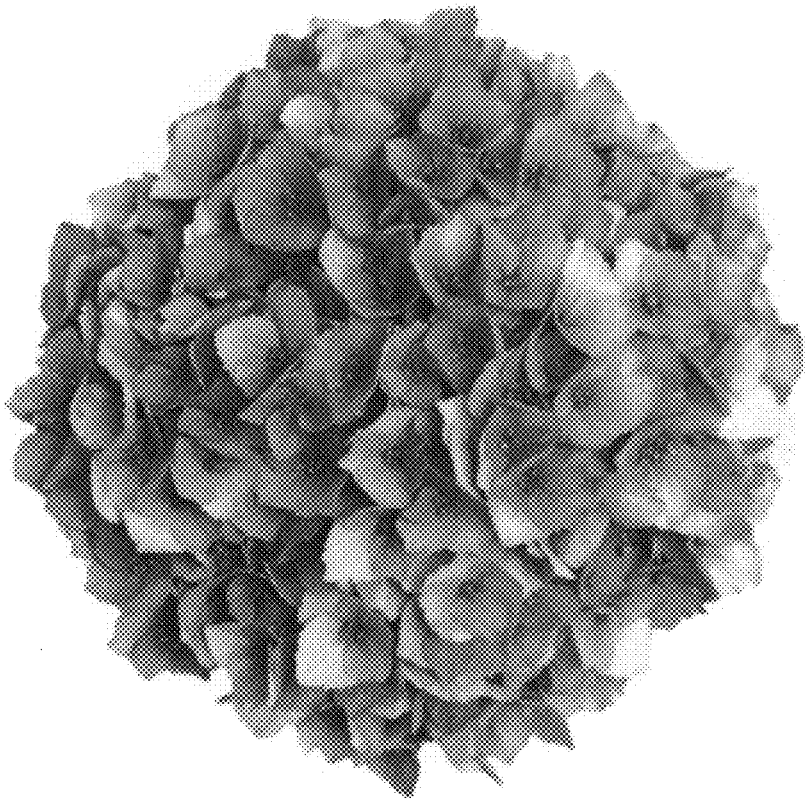

The photograph on the third sheet (FIG. 3 of 3) is a close-up view of a typical inflorescence of 'SCHROLL66-11-01' that has been "blued".

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched two times and were one year old when the photographs and description were taken. During the production of the plants, day temperatures ranged from 15° C. to 25° C. and night temperatures ranged from 10° C. to 20° C. and light levels ranged from 40 to 50 klux. In the following description, color references are made to The Royal Horticultural Society Colour Chart, 2007 Edition, except where general terms of ordinary dictionary significance are used.

Botanical description: *Hydrangea macrophylla* 'SCHROLL66-11-01'.

Parentage:

*Female, or seed, parent*.—Proprietary selection of *Hydrangea macrophylla* identified as code number 36-00, not patented.

*Male, or pollen, parent*.—Proprietary selection of *Hydrangea macrophylla* identified as code number 083001, not patented.

Propagation:

*Type cutting*.—By softwood cuttings.

*Time to initiate roots, summer*.—About two weeks at temperatures about 19° C. to 22° C.

*Time to initiate roots, winter*.—About 17 days at temperatures about 18° C. to 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to 158C, in color.

*Rooting habit*.—Freely branching; medium density.

Plant description:

*Plant and growth habit*.—Perennial subshrub; compact, upright and mounded plant habit; broadly inverted triangle; freely branching habit with about four to six lateral branches developing per plant; strong lateral branches; moderately vigorous growth habit and relatively slow growth rate.

*Plant height*.—About 23 cm to 28 cm.

*Plant diameter or area of spread*.—About 27 cm to 32 cm.

*Lateral branches*.—Length: About 22 cm to 27 cm. Diameter: About 5 mm to 7 mm. Internode length: About 3 cm to 5 cm. Strength: Strong, sturdy; flexible. Texture: Pubescent. Color, developing: Close to 143C. Color, developed: Close to 143C; distally, close to N187A to N187B. Lenticels: Sparse; about 0.5 mm to 1 mm in length and close to 187C in color.

Leaf description:

*Arrangement*.—Opposite, decussate; simple.

*Length*.—About 9 cm to 15 cm.

*Width*.—About 6 cm to 9 cm.

*Shape*.—Ovate.

*Apex*.—Acuminate to cuspidate.

*Base*.—Acute to obtuse.

*Margin*.—Denticulate to serrulate.

*Texture, upper surface*.—Smooth to rugose, glabrous; slightly undulate.

*Texture, lower surface*.—Rugose, glabrous.

*Venation pattern*.—Pinnate, reticulate.

*Color*.—Developing leaves, upper surface: Close to 137A. Developing leaves, lower surface: Close to 138B. Fully expanded leaves, upper surface: Close to N137A; venation, close to 143D. Fully expanded leaves, lower surface: Close to 138B and 138C; venation, close to 142B.

*Petioles*.—Length: About 1.5 cm to 2 cm. Diameter: About 3 mm. Strength: Strong. Texture, upper and lower surfaces: Smooth, glabrous. Color, upper surface: Close to 141C. Color, lower surface: Close to 142B.

Inflorescence & flower description:

*Flower type and habit*.—Showy single sterile and inconspicuous single fertile flowers arranged on terminal mophead-type panicles; panicles flattened globular in overall shape; fertile flowers face upright and sterile flowers face mostly upright to outwardly depending on their position on the inflorescence; moderate flowering habit, plants begin flowering about ten to twelve weeks after forcing period.

*Natural flowering season*.—Long flowering period, continuous flowering from late summer (August) until frost in Northern Europe.

*Flower longevity, fertile flowers*.—Flowers last less than one month on the plant; fertile flowers not persistent.

*Flower longevity, sterile flowers*.—Flowers last about six months on the plant; sterile flowers persistent.

*Quantity of flowers*.—Freely flowering habit with about 15 to 20 fertile flowers and about 120 to 150 sterile flowers per panicle.

*Fragrance*.—Faint to moderate; sweet, pleasant.

*Panicle height*.—About 5 cm to 7 cm.

*Panicle diameter*.—About 13 cm to 16 cm.

*Flower diameter, fertile flowers*.—About 8 mm to 10 mm.

*Flower depth (height), fertile flowers*.—About 5 mm to 7 mm.

*Flower diameter, sterile flowers*.—About 3.5 cm to 4.5 cm.

*Flower depth (height), sterile flowers*.—About 1 cm to 1.5 cm.

*Flower shape, fertile flowers*.—Spherical.

*Flower shape, sterile flowers*.—Oval-shape diamond.

*Flower buds, fertile flowers*.—Length: About 3 mm. Diameter: About 3 mm. Shape: Spherical. Color: Close to 143C; when "blued", close to 77C.

*Flower buds, sterile flowers*.—Length: About 2 mm. Diameter: About 2 mm. Shape: Spherical. Color: Close to 143B.

*Petals, fertile flowers*.—Quantity and arrangement: Five in a single whorl. Length: About 5 mm. Width: About 3 mm. Shape: Ovate. Apex: Acute. Base: Obtuse to truncate. Margin: Entire. Texture, upper and lower surfaces: Smooth, glabrous. Color: When opening, upper surface: Close to 77B; when "blued", close to 96B. When opening, lower surface: Close to 77C; when "blued", close to 96B. Fully opened, upper surface: Close to 77A; when "blued", close to 96C; color does not change with development. Fully opened, lower surface: Close to N77B; when "blued", close to 96C; color does not change with development.

*Petals, sterile flowers*.—Quantity and arrangement: About eight to ten in about two whorls. Length: About 3 mm to 4 mm. Width: About 2 mm. Shape: Ovate. Apex: Acute. Base: Obtuse. Margin: Entire. Texture, upper and lower surfaces: Smooth, glabrous. Color: When opening, upper surface: Close to 68C; when "blued", close to 96D. When opening, lower surface: Close to 70C; when "blued", close to 96C. Fully opened, upper surface: Close to 70C; when "blued", close to 96D; color becoming closer to N74D with development and when "blued", close to 98A. Fully opened, lower surface: Close to 70C; when "blued", close to 96C; color becoming closer to N74D with development and when "blued", close to 98A.

*Sepals, fertile flowers*.—Quantity and arrangement: About five in a single whorl. Length: About 1 mm to 2 mm. Width: About 1 mm. Shape: Ovate. Apex: Acute. Base: Cuneate. Margin: Entire. Texture, upper surface: Smooth, glabrous. Texture, lower surface: Pubescent. Color: When opening, upper surface: Close to 154C; when "blued", close to 150A. When opening, lower surface: Close to 149C; when "blued", close to 150C. Fully opened, upper surface: Close to N144D; when "blued", close to 101C, colors do not change with development. Fully opened, lower surface: Close to N144D; when "blued", close to 101D; colors do not change with development.

*Sepals, sterile flowers*.—Quantity and arrangement: Four in a single whorl. Length: About 2.5 cm to 3 cm. Width: About 2.5 cm to 3 cm. Shape: Deltoid to reniform, slightly curved. Apex: Acute. Base: Cuneate. Margin: Crenate. Texture, upper surface: Smooth, glabrous. Texture, lower surface: Slightly rugose, glabrous. Color, plants not "blued": When opening, upper surface: Initially, close to 145C and towards the margins, close to N66C; with development, becoming closer to 69C and towards the margins, marks, close to 73A. When opening, lower surface: Initially, close to 145B; with development, becoming closer to 69D. Fully opened, upper surface: Close to N57D. Fully opened, lower surface: Close to 62C. Color, plants "blued": When opening, upper surface: Initially, close to 149D; with development, becoming closer to 97A and towards the base, fading to close to 97D. When opening, lower surface: Initially, close to 150D; with development, becoming closer to 97B and towards the base, fading to close to 97D. Fully opened, upper surface: Close to 96B. Fully opened, lower surface: Close to 98B.

*Pedicels, fertile flowers*.—Length: About 4 mm to 7 mm. Diameter: About 1 mm. Strength: Strong. Aspect: Mostly upright. Texture: Slightly ridged; pubescent. Color: Close to 77B; when "blued", close to 98A.

*Pedicels, sterile flowers*.—Length: About 1 cm to 2 cm. Diameter: About 1 mm to 2 mm. Strength: Strong. Aspect: Erect to horizontal. Texture: Pubescent. Color: Close to N57C; when "blued", close to 98A.

*Reproductive organs, fertile flowers*.—Stamens: Quantity per flower: About ten. Filament length: About 4 mm to 5 mm. Filament color: Close to 77A; when "blued", close to 96A. Anther length: About 1 mm. Anther shape: Oval. Anther color: Close to 150D; when "blued", close to 96B. Pollen amount: Abundant. Pollen color: Close to 150D. Pistils: Pistil quantity per flower: About three. Pistil length: About 1 mm. Stigma shape: Oval. Stigma color: Close to 77A; when "blued", close to 96A. Style length: About 1 mm. Style color: Close to 77C; when "blued", close to 98C. Ovary color: Close to 155D.

*Reproductive organs, sterile flowers*.—Stamens: Quantity per flower: If present, about three to four. Filament length: About 5 mm. Filament color: Close to 64A; when "blued", close to 96A. Anther length: About 1 mm. Anther shape: Oval. Anther color:

Close to N77D; when "blued", close to 98B. Pollen amount: Abundant. Pollen color: Close to 150D. Pistils: Pistil quantity per flower: Two. Pistil length: About 1 mm. Stigma shape: Oval. Stigma color: Close to 71A; when "blued", close to 98A. Style length: About 1 mm. Style color: Close to 70B; when "blued", close to 98B. Ovary color: Close to 70A; when "blued", close to 101D.

*Seeds* (*developing on fertile flowers only*).—Quantity per fertile flower: About 50. Length: About 0.5 mm. Diameter: About 0.1 mm. Color: Close to 200C.

Pathogen & pest resistance: To date, plants of the new *Hydrangea* have not been observed to be resistant to pathogens and pests common to *Hydrangea* plants.

Temperature tolerance: Plants of the new *Hydrangea* have been shown to be tolerant to temperatures ranging from about −5° C. to 38° C.

It is claimed:

1. A new and distinct *Hydrangea* plant named 'SCHROLL66-11-01' as illustrated and described.

* * * * *